(12) United States Patent
Kandel et al.

(10) Patent No.: US 7,874,675 B2
(45) Date of Patent: *Jan. 25, 2011

(54) PUPILLARY REFLEX IMAGING

(75) Inventors: Gillray L. Kandel, Troy, NY (US); Martin B. Kaback, Slingerlands, NY (US)

(73) Assignee: Konan Medical USA, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/367,916

(22) Filed: Feb. 9, 2009

(65) Prior Publication Data

US 2009/0147218 A1  Jun. 11, 2009

Related U.S. Application Data

(63) Continuation of application No. 11/873,296, filed on Oct. 16, 2007, now Pat. No. 7,488,073, which is a continuation of application No. 10/641,435, filed on Aug. 15, 2003, now Pat. No. 7,334,895.

(60) Provisional application No. 60/404,000, filed on Aug. 16, 2002, provisional application No. 60/404,232, filed on Aug. 16, 2002.

(51) Int. Cl.
A61B 3/10 (2006.01)
(52) U.S. Cl. .................................. 351/221; 351/246
(58) Field of Classification Search .......... 351/221, 351/246, 243, 205, 213, 200, 233; 600/558; 359/630, 631; 362/347, 350
See application file for complete search history.

(56) References Cited

U.S. PATENT DOCUMENTS

| | | | |
|---|---|---|---|
| 2,573,464 A | 10/1951 | Lowenstein et al. | |
| 3,036,568 A | 5/1962 | Stark | |
| 3,533,683 A | 10/1970 | Stark et al. | |
| 3,533,684 A | 10/1970 | Stark et al. | |
| 3,639,041 A | 2/1972 | Cornsweet | |
| 3,770,342 A | 11/1973 | Dudragne | |
| 3,966,310 A | 6/1976 | Larson | |
| 4,012,128 A | 3/1977 | Regan | |
| 4,208,107 A | 6/1980 | Oharek | |
| 4,651,257 A | 3/1987 | Gehly | |
| 4,755,043 A | 7/1988 | Carter | |

(Continued)

FOREIGN PATENT DOCUMENTS

JP  404317624 A  11/1992

(Continued)

OTHER PUBLICATIONS

U.S. Appl. No. 11/873,296, Notice of Allowance, Oct. 2, 2008, 8 pages.

(Continued)

*Primary Examiner*—Hung X Dang
(74) *Attorney, Agent, or Firm*—John W. LaBatt; Hoffman Warnick LLC

(57) ABSTRACT

A method, system and device for recording image data for a pair of eyes exposes to a series of flashes that includes flashes that vary chromatically is provided. More particularly, one eye is exposed to the series of flashes, and the resulting pupillary reflexes of both eyes are concurrently recorded.

24 Claims, 9 Drawing Sheets

U.S. PATENT DOCUMENTS

| | | | |
|---|---|---|---|
| 4,822,162 | A | 4/1989 | Richardson et al. |
| 4,850,691 | A | 7/1989 | Gardner et al. |
| 5,042,937 | A | 8/1991 | Cornsweet |
| 5,065,767 | A | 11/1991 | Maddess |
| 5,141,305 | A | 8/1992 | Young |
| 5,187,506 | A | 2/1993 | Carter |
| 5,237,349 | A | 8/1993 | Burckhardt |
| 5,295,495 | A | 3/1994 | Maddess |
| 5,490,098 | A | 2/1996 | Kardon |
| 5,506,633 | A | 4/1996 | Sperling |
| 5,539,482 | A | 7/1996 | James et al. |
| 5,609,159 | A | 3/1997 | Kandel et al. |
| 5,632,282 | A | 5/1997 | Hay et al. |
| 5,646,709 | A | 7/1997 | Carter |
| 5,661,538 | A | 8/1997 | Carter |
| 5,784,145 | A | 7/1998 | Ghodse et al. |
| 5,883,691 | A | 3/1999 | Ishikawa et al. |
| 5,892,568 | A | 4/1999 | Carter |
| 5,912,723 | A | 6/1999 | Maddess |
| 5,956,125 | A | 9/1999 | Rosse et al. |
| 6,086,206 | A | 7/2000 | Sutter |
| 6,162,186 | A | 12/2000 | Scinto et al. |
| 6,315,414 | B1 | 11/2001 | Maddess et al. |
| 6,382,792 | B1 | 5/2002 | Khoury |
| 6,497,483 | B2 | 12/2002 | Frey et al. |
| 6,561,648 | B2 | 5/2003 | Thomas |
| 6,644,810 | B1 | 11/2003 | Ulbers |
| 6,669,651 | B1 | 12/2003 | Fukushima et al. |
| 6,702,757 | B2 | 3/2004 | Fukushima et al. |
| 6,820,979 | B1 | 11/2004 | Stark et al. |
| 6,879,443 | B2 | 4/2005 | Spitzer et al. |
| 7,006,863 | B2 | 2/2006 | Maddess et al. |
| 7,334,895 | B2 * | 2/2008 | Kandel et al. ............... 351/221 |
| 7,488,073 | B2 * | 2/2009 | Kandel et al. ............... 351/221 |
| 2002/0024633 | A1 | 2/2002 | Kim et al. |

FOREIGN PATENT DOCUMENTS

| | | | |
|---|---|---|---|
| JP | 2002034926 A | 2/2002 | |

OTHER PUBLICATIONS

U.S. Appl. No. 11/873,296, Amendment To Office Action, Aug. 8, 2008, 6 pages.

U.S. Appl. No. 11/873,296, Office Action, May 2, 2008, 15 pages.

Johnson, "The Relative Afferent Pupillary Defect and a Novel Method of Fusion Recovery With the Worth 4-Dot Test," American Medical Association, Archives of Opthalmology, vol. 114, Feb. 1996, p. 171.

Thompson et al., "Asymmetry of Pupillomotor Input," Neuro-opthalmology Unit, Departments of Opthalmology and Neurology, University of Iowa, 1991, 1 page.

Maxner, "Pupil Disorders," Neuro-opthalmology Course, Camp Hill Medical Centre, Dalhousie University, Halifax, Nova Scotia, Jun. 19, 1991, pp. 1-12.

Adams et al., "New Clinical Color Threshold Test for Eye Disease," American Journal of Optometry and Physiological Optics, vol. 64, No. 1, pp. 29-37.

Adams et al., "Clinical Measures of Central Vision Function in Glaucoma and Ocular Hypertension," Archives of Opthalmology, vol. 105, Jun. 1987, pp. 782-787.

Young et al., "Screening of Red-Green Color-Deficient Observers Using the Chromatic Pupillary Response," Clinical Vision Science, vol. 2, No. 2, 1987 pp. 117-122.

Young et al., "Pupil responses to foveal exchange of monochromatic lights," Optical Society of America, vol. 70, No. 6, Jun. 1980, pp. 697-706.

Riggs et al., "Electrical Responses of the Human Eye to Changes in Wavelength of the Stimulating Light," Journal of the Optical Society of America, vol. 56, No. 11, Nov. 1996, pp. 1621-1625.

PCT Search Report, PCT/US03/25550, Feb. 11, 2004, 3 pages.

U.S. Appl. No. 10/641,435, 312 Amendment, Aug. 7, 2007, 8 pages.

U.S. Appl. No. 10/641,435, Notice of Allowance, May 11, 2007, 6 pages.

U.S. Appl. No. 10/641,435, Amendment to Office Action, Oct. 20, 2006, 16 pages.

U.S. Appl. No. 10/641,435, Office Action, Jun. 22, 2006, 10 pages.

EP03788506; Supplementary Partial European Search Report; Mar. 2, 2009; 4 pages.

Vanderperren, Y., "Communication pursuant to Article 94(3) EPC," Jun. 22, 2009, pp. 1-5.

EPO, "Communication pursuant to Article 94(3) EPC", Dated Mar. 26, 2010, 4 pages.

* cited by examiner

RIGHT EYE VS. RIGHT EYE

|   | B | A | P | N | L | S | J | O | Y |
|---|---|---|---|---|---|---|---|---|---|
| B | 1 | 0.425 |   |   |   |   |   |   |   |
| A |   | 1 | 0.581 |   |   |   | 0.498 |   |   |
| P |   |   | 1 |   |   |   | 0.481 |   |   |
| N |   |   |   | 1 |   |   |   |   |   |
| L |   |   |   |   | 1 |   |   |   |   |
| S |   |   |   |   |   | 1 |   |   |   |
| J |   |   |   |   |   |   | 1 |   | 0.417 |
| O |   |   |   |   |   |   |   | 1 | 0.504 |
| Y |   |   |   |   |   |   |   |   | 1 |

FIG. 8A

LEFT EYE VS. LEFT EYE

|   | B | A | P | N | L | S | J | O | Y |
|---|---|---|---|---|---|---|---|---|---|
| B | 1 |   |   |   |   | 0.604 |   |   |   |
| A |   | 1 |   |   |   | 0.657 |   | 0.462 |   |
| P |   |   | 1 |   |   |   |   |   |   |
| N |   |   |   | 1 |   |   |   |   |   |
| L |   |   |   |   | 1 |   |   |   |   |
| S |   |   |   |   |   | 1 |   |   |   |
| J |   |   |   |   |   |   | 1 |   |   |
| O |   |   |   |   |   |   |   | 1 |   |
| Y |   |   |   |   |   |   |   |   | 1 |

FIG. 8B

RIGHT EYE (PATIENTS ON SIDE) VS. LEFT EYE (PATIENTS ON TOP)

|   | B | A | P | N | L | S | J | O | Y |
|---|---|---|---|---|---|---|---|---|---|
| B | 0.578 |   |   |   |   |   |   |   | 0.420 |
| A |   |   | 0.736 |   |   |   |   |   |   |
| P |   |   | 0.817 |   |   |   |   |   |   |
| N |   |   |   |   | 0.477 |   |   |   |   |
| L |   |   |   |   |   |   |   |   |   |
| S |   | 0.487 |   | 0.494 |   | 0.576 |   |   |   |
| J |   |   | 0.695 |   |   |   | 0.795 |   |   |
| O |   |   |   |   |   |   |   |   |   |
| Y |   |   |   |   |   |   |   |   | 0.827 |

FIG. 8C

*ONLY POSITIVE INERCORRELATIONS REACHING P=0.055 ON A ONE TAILED TEST ARE SHOWN

PUPILLARY REFLEX IMAGING

REFERENCE TO PRIOR APPLICATIONS

This application is a continuation of U.S. patent application Ser. No. 11/873,296, now U.S. Pat. No. 7,488,073, which was filed on 16 Oct. 2007, which is a continuation of U.S. Utility patent application Ser. No. 10/641,435, now U.S. Pat. No. 7,334,895, which was filed on 15 Aug. 2003, and which claims the benefit of co-pending U.S. Provisional Application Ser. No. 60/404,000 and U.S. Provisional Application Ser. No. 60/404,232, both filed on 16 Aug. 2002, all of which are hereby incorporated herein by reference.

BACKGROUND OF THE INVENTION

1. Technical Field

The invention generally relates to a method, system and device for obtaining data that can be used to detect ocular dysfunctions. More particularly, the invention provides a method, system and device for exposing one or both eyes to a series of light flashes and measuring the direct and/or consensual pupillary reflexes that can be used to detect the presence of various dysfunctions and/or disorders.

2. Background Art

During eye examinations, the pupillary reflexes of a patient are often monitored to determine the presence of various ocular dysfunctions. The presence of one or more ocular dysfunctions can signal that the patient suffers from an ocular disorder such as optic neuropathy, other pathology of the ocular pathways between the photoreceptors of the retina and brain, opacification of the ocular media, or conditions that impact the transmission of light through the ocular media. A common objective visual functional test for the detection of such visual dysfunctions is the "Swinging Flashlight Test" (SFT). For the SFT, a handheld, very bright light source is shined first into one eye of the patient and then into the other eye, in a pendular fashion with a period of one to two seconds. While this is being done, the examiner will observe the reflexes of the patient's pupils. A detection of a positive sign is made based on the observed reflexes.

For example, if the light is shined into an eye that has an optic nerve conduction defect, while the other eye does not, the pupil of the eye with the defect, will contract to a lesser degree than will the pupil of the eye without the defect when that eye is stimulated with the same light. Similarly, if both eyes have a defect, one having a greater defect than the other, the light being shined into the eye with the greater defective optic nerve will evoke a lesser pupillary contraction of both pupils than would the same light shown into the eye with the lesser optic nerve defect, thus yielding the sign of a Relative Afferent Pupillary Defect (RAPD). Moreover, in the presence of a RAPD, when the light is alternated every few seconds between the two eyes, these differences in pupillary reflexes to the same bright light shined into the two eyes may give rise to an "illusion" that shining the same bright light into the eye with the greater defect caused its pupil to dilate (or expand), a so called Marcus-Gunn pupil.

The SFT is a foremost example of an objective functional test of the visual system that depends upon differences in pupillary reflexes to infer the presence of an ocular dysfunction, and therefore an ocular disorder (i.e., disease or pathology). However, this test has numerous drawbacks. In particular, it lacks specificity for any one ocular disorder whether of neurological or transmissive origin. It can be positive in unilateral dense cataracts, in certain unilateral retinal disorders, in anisocoria, as well as in significant asymmetric glaucoma. The clinician can not tell which ocular disorder is present based on the pupillary reflexes alone. Moreover, the SFT lacks sensitivity due to the manner in which the differences between the direct and consensual reflexes are observed. For example, the clinician can not observe the pupils of both eyes simultaneously, but must visualize the reflex of one pupil first and then visualize the reflex of the other pupil moments later. As a result, small differences in reflexes may go unnoticed. The unaided observation makes this comparative judgement subject to significant error and makes the detection of small differences in reflexes between the two eyes especially problematic. Because the SFT relies on the examiner's naked eye to detect and diagnose ocular dysfunctions, it lacks practical utility. Moreover, by depending on a single bright light, the SFT stimulates the visual system in an indiscriminate manner. As a result, this manner of evoking the pupils' reflexes, has proven to be lacking in both sensitivity and specificity.

Further, several observations have been made concerning the ocular disorder glaucoma, thought to be a form of optic neuropathy. First, glaucoma and glaucoma suspect patients display a significant degree of dyschromatopsia, i.e., deficiencies in color discrimination. Second, patients with asymmetric glaucoma, as measured by visual field loss and cup-disc ratios, manifest gross afferent pupillary defects to a greater extent than do patients without glaucoma. Third, a consensual pupillary reflex can be induced by the interchange of equally luminous, heterochromatic members of a pair of monochromatic lights shined into the patient's contralateral eye. This finding must mean that chromatic differences in stimuli, activate pupillary reflexes via stimulation of different cell populations independently of the luminosity change that is thought to be the primary basis of the pupillary reflex activation in the SFT.

Although not previously brought to bear on detecting specific ocular dysfunctions, attempts have been made to solve these problems by implementing systems and devices for measuring pupillary reflexes to light stimuli. Such devices generally implement a system for exposing a patient's eyes to stimuli and then measuring the pupillary reaction thereof In particular, the goal is to intentionally induce a pupillary reflex and then measure the reflex using various means. Since dimensional changes in the pupil's movements can often be minuscule, the comparison to a range of "normal" reactions obtained from different patients can lack accuracy. Without an appropriate validation procedure, this could lead to either a false diagnosis of a disorder that is not present, a failure to diagnose a disorder that is present, or a failure to distinguish between two ocular diseases. Furthermore, if the examiner is seeking specific information, for example, about the afferent optic nerve pathology of a patient, efferent deficiencies may significantly confound the interpretation of such sought for information.

Therefore there exists a need for a method and device that allow for the sensitive and accurate recordation and/or comparison of the pupillary reflexes of a patient's eyes to a series of flashes that target specific cell populations of the visual system. Moreover, there is a need for a method, system and device that are able to differentiate between various asymmetries of afferent or efferent origin, whether revealed in the afferent or the efferent branches of the pupillomotor system, and whether they be of retinal, ocular, illuminometric, or optic nerve origin.

SUMMARY OF THE INVENTION

The invention provides a method, system and device for obtaining data that can be used to detect an ocular dysfunction in a patient. In particular, a first eye is exposed to a series of flashes in which each flash varies chromatically from the other flashes in the series. Pupillary reflexes for both eyes are measured during the exposures. The pupillary reflexes can then be evaluated to determine if an ocular dysfunction is present. In one embodiment, both eyes are alternately exposed to the same series of flashes. Further, additional series of flashes that vary by location in the visual field and/or luminosity (i.e., brightness) can be incorporated and evaluated.

A first aspect of the invention provides a method of detecting an ocular dysfunction in a patient, the method comprising the steps of: exposing a first eye to a first series of flashes, wherein each flash in the first series of flashes varies chromatically from the other flashes; concurrently measuring pupillary reflexes of the first eye and a second eye of the patient during the exposing step; and evaluating the pupillary reflexes to determine if the ocular dysfunction is present.

A second aspect of the invention provides a method of detecting an ocular dysfunction in a patient, the method comprising the steps of: exposing a first eye of the patient to a series of flashes generated by a first light source, wherein each flash in the series of flashes varies chromatically from the other flashes in the series of flashes; exposing a second eye of the patient to the series of flashes generated by a second light source; altering a luminosity of the first and second light sources; repeating the exposing steps using the altered luminosities; altering a location of the first and second light sources in the visual fields of the first and second eyes; repeating the exposing steps using the altered locations; concurrently recording pupillary reflexes of the first eye and the second eye during each exposing step; and evaluating the recorded pupillary reflexes to determine if the ocular dysfunction is present.

A third aspect of the invention provides a system for detecting an ocular dysfunction, comprising: a first eye scope for exposing a first eye to a series of flashes and detecting a pupillary reflex of the first eye for each flash, the first eye scope having an ocular aperture, a light aperture, and a monitoring aperture; a second eye scope for detecting a pupillary reflex of a second eye for each flash, the second eye scope having an ocular aperture and a monitoring aperture; a first light source for generating the series of flashes through the light aperture, wherein each flash in the series of flashes varies chromatically from the other flashes; and a measurement system for concurrently measuring the pupillary reflexes of the first eye and the second eye based on light passing through the monitoring apertures.

A fourth aspect of the invention provides a device for detecting an ocular dysfunction, comprising: a first eye scope for exposing a first eye to a series of flashes and detecting a pupillary reflex of the first eye for each flash, the first eye scope having an ocular aperture, a light aperture, and a monitoring aperture; a second eye scope for detecting a pupillary reflex of a second eye for each flash, the second eye scope having an ocular aperture and a monitoring aperture; and a first light source for generating the series of flashes through the light aperture, wherein each flash in the series of flashes varies by at least one of: chromatically, location in the visual field, and luminosity from the other flashes in the series of flashes.

A fifth aspect of the invention provides a device for detecting ocular dysfunctions that comprises: (1) a light emitting sphere having: (a) an exit port; (b) an outer portion positioned along a periphery of the exit port, wherein the outer portion has a light source disposed thereon; and (c) a reflective well portion, wherein light emitted from the light source shines from the outer portion to the reflective well portion, and wherein the light reflects off the reflective well portion and exits the light emitting sphere through the exit port as a single beam of light.

The illustrative aspects of the invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which:

FIG. 8 shows an illustrative set of inter-correlation matrices constructed according to yet another aspect of the invention.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As stated above, the invention provides a method, system and device for obtaining data that can be used to detect an ocular dysfunction in a patient. In particular, a first eye is exposed to a series of flashes in which each flash varies chromatically from the other flashes in the series. Pupillary reflexes for both eyes are measured during the exposures. The pupillary reflexes can then be evaluated to determine if an ocular dysfunction is present. In one embodiment, both eyes are alternately exposed to the same series of flashes. Further, additional series of flashes that vary by location in the visual field and/or luminosity (i.e., brightness) can be incorporated and evaluated.

As a result, the invention can target different visual functions and cell populations by incorporating series of flashes that vary chromatically, luminosity, and/or by location in the visual field. Each flash comprises a beam of light having a short time duration. In one embodiment, each flash is terminated before the release (escape) phase of the pupillary reflex has begun, for example, after approximately 0.6 seconds. This allows for a substantial increase in the number of distinct afferent and efferent reflex pathways that can be probed by using the invention rather than the SFT. By probing a larger number of pathways, a highly discriminative and sensitive measure of any optic neuropathology that may manifest itself in any of the different conductive ocular pathway pathologies can be obtained, and permits a separate assessment of efferent pathology. The data provided by the series of flashes can be processed to detect afferent optic nerve or efferent pupillary asymmetry. Further, the data can provide a direction sensitive measurement of pupillary reflexes in both eyes. Consequently, the invention can provide sufficiently sensitive measurements to evaluate asymmetric precursory manifestations (i.e., ocular dysfunctions) of any ocular disorder that is bilateral in nature. For example, ocular dysfunctions that occur in disorders such as the glaucoma group of eye diseases, optic neuritis, retinal pathologies, etc. can be detected using the present invention.

Figure 1A:
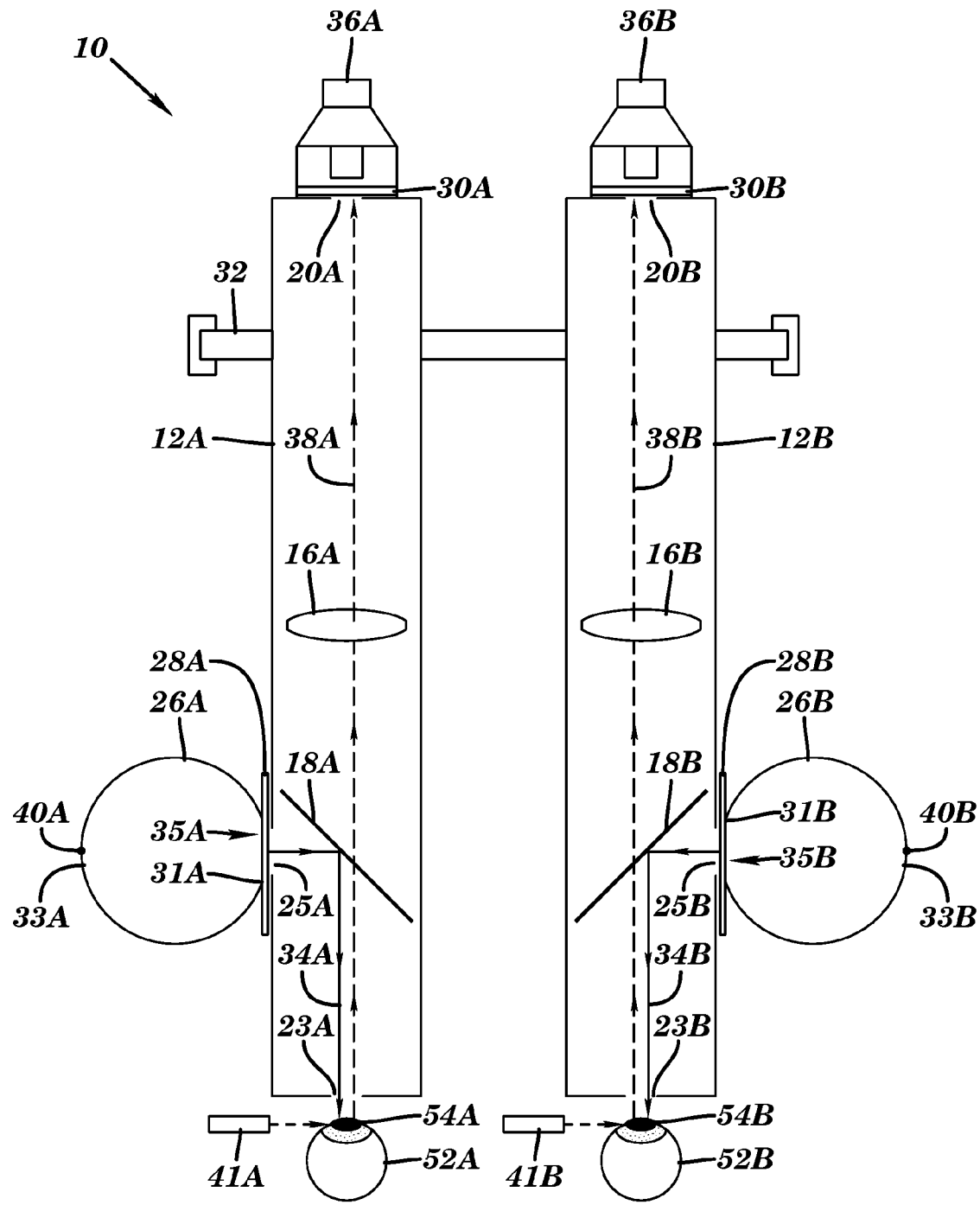
FIG. 1A is a top view of a device according to one aspect of the invention.
Figure 1B:
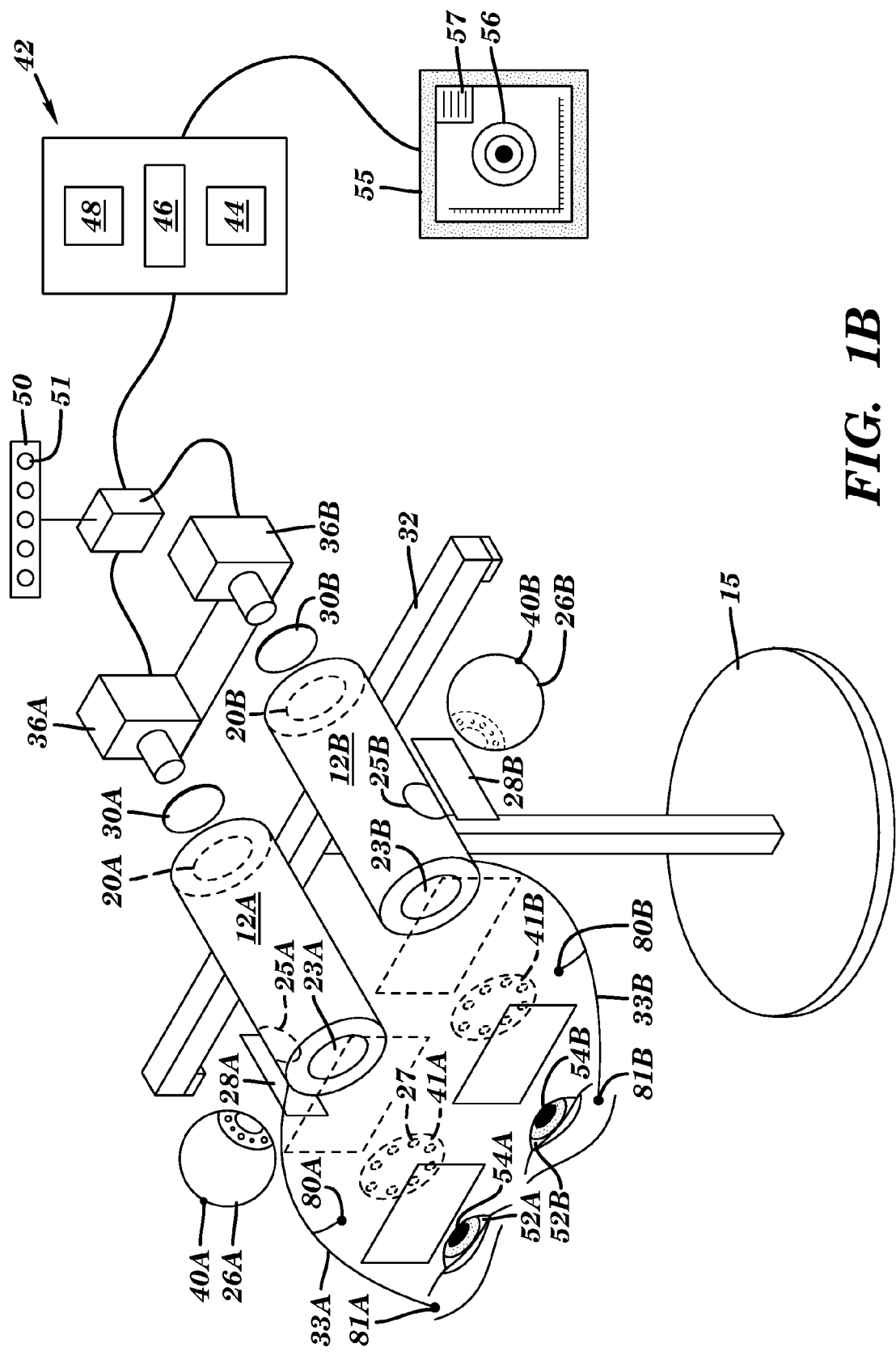
FIG. 1B is perspective view of a system that includes the device shown in FIG. 1A according to another aspect of the invention.

Turning to the drawings, FIG. 1A shows a device 10 for exposing an eye 52A-B to a series of flashes and FIG. 1B shows device 10 when implemented as part of a system for detecting an ocular disorder. In FIG. 1A, device 10 is shown including a pair of eye scopes 12A-B. Each eye scope 12A-B is shown including an ocular aperture 23A-B, a monitoring aperture 20A-B, and a light aperture 25A-B. Further, mirrors 18A-B, and achromatic lenses 16A-B are shown disposed within eye scopes 12A-B, and light sources 26A-B are shown positioned proximate to light apertures 25A-B in eye scopes 12A-B. To test a patient's eyes 52A-B, the patient places both eyes 52A-B so that light passing out of eye scopes 12A-B through ocular apertures 23A-B will enter the eyes 52A-B. Subsequently, one of light sources 26A-B generates a series of flashes (i.e., multiple brief instances of light) that pass through the corresponding light aperture 25A-B, are reflected by the corresponding mirror 18A-B, and pass through the corresponding ocular aperture 23A-B along path 34A-B in the direction shown. As each flash passes through the ocular aperture 23A-B, the corresponding pupil 54A-B of the eye 52A-B responds by adjusting to a certain size/position.

To assist in correctly placing eyes 52A-B for testing, eye scopes 12A-B are shown mounted on an interocular distance adjuster 32. Interocular distance adjuster 32 can be used to adjust the distance between eye scopes 12A-B to correspond with the distance between a particular patient's eyes 52A-B. Further, FIG. 1B shows interocular distance adjuster 32 mounted to a support mechanism 15. In addition to providing stability to eye scopes 12A-B, support mechanism 15 can provide upward and downward adjustments of eye scopes 12A-B. FIG. 1B also shows device 10 including head holder frames 33A-B that include sensor switches 80A-B, 81A-B. Head holder frames 33A-B can assist in holding a patient's head in its desired position during testing, while sensor switches 80A-B, 81A-B can generate a signal (e.g., illuminate a light) when the patient's head is in the desired position for testing. The location of sensor switches 80A-B, 81A-B can be adjusted to conform to various head sizes.

Figure 2:
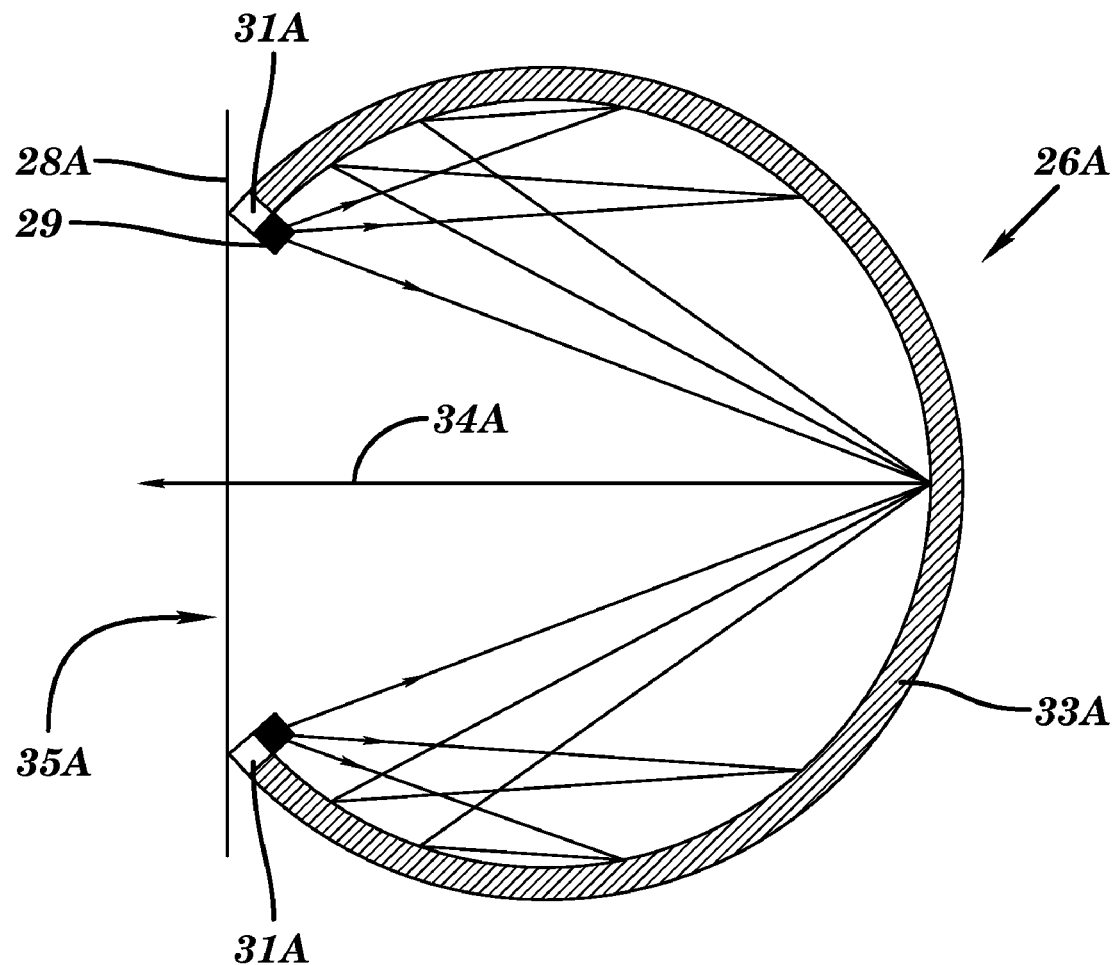
FIG. 2 is a cross-sectional view of a light emitting sphere according to still another aspect of the invention.

As discussed, an eye 52A-B is exposed to a series of flashes generated by one of light sources 26A-B during testing. It is understood that device 10 could include a single light source 26A that generates the series of lights for both eye scopes 12A-B. For example, light source 26A could be moved between eye scopes 12A-B, a system of movable mirrors could be implemented, etc. In one embodiment, each light source 26A-B comprises a light emitting sphere. FIG. 2 shows a preferred embodiment for light emitting sphere 26A adjacent eye scope 12A (FIG. 1A). It is understood that light emitting sphere 26B adjacent eye scope 12B is similar and, accordingly, has like elements. As shown, light emitting sphere 26A comprises an outer portion 31A, a reflective well portion 33A, and an exit port 35A. Disposed along outer portion 31A are a plurality of monochromatic light sources 29 and, optionally, infrared light sources (e.g., light emitting diodes (LEDs)). In one embodiment, monochromatic light sources 29 positioned about the outer portion 31A, comprise at least four different, non-spectrally-adjacent hues. For example, monochromatic light sources 29 can include light sources 29 that generate hues and corresponding peak emission wavelengths that correspond to blue (approximately 430 nanometers), green (approximately 560 nanometers), yellow (approximately 585 nanometers), and red (approximately 660 nanometers). It is understood, however, that other differing peak emission wavelengths, may be incorporated.

As further shown in FIG. 2, monochromatic light sources 29 point inward toward reflective body portion 33A. As a result, the light emitted from each monochromatic light source 29 shines into sphere 26A, reflects throughout reflective well portion 33A and eventually reflects back through exit port 35A as a single beam of light 34A in aperture mode. As beam of light 34A passes through exit port 35A, it may pass through a polarizing screen 28A. Polarizing screen 28A can be used to reduce any light artifact when testing a patient under the bright conditions. It is understood that the light will be reflected throughout the entire reflective well portion 33A. The limited number of reflections shown in FIG. 2 is for clarity of illustration.

The use of reflected monochromatic light presented in aperture mode instead of direct monochromatic light provides uniformly intense illumination of a limited region of the patient's visual field. Moreover, the use of reflected light is advantageous because no single light source 29, when flashed, may be intense enough to generate a pupillary reflex by pupil 54A-B by itself Therefore, in order to produce enough stimulus intensity to drive the pupil's reflexes, several monochromatic LED sources 29 can be "combined" (integrated) by light emitting sphere 26A-B to form beam of light 34A on which the patient's eyes 52A-B should be fixated.

Referring back to FIGS. 1A and 1B, light sources 26A-B may also each include a fixation point 40A-B to which the patient can direct his/her gaze as is known in the art. Fixation points 40A-B provide a central point on which patients should focus while looking into eye scopes 12A-B through ocular apertures 23A-B. When focused on a central point, the testing procedures, described in more detail below, are more accurately performed because the patient's eyes 52A-B do not wander. Each fixation point 40A-B can be provided by two single light sources, via beam splitters, etc. Such fixation arrangements are well known in the art.

The pupillary reflexes of both eyes 52A-B are measured while one eye 52A-B is being exposed to the series of flashes. To assist in measuring the pupillary reflexes of eyes 52A-B, device 10 is also shown in FIG. 1A as including a pair of light sources 41A-B and a pair of achromatic lenses 16A-B. Light from light sources 41A-B reflects off of eyes 52A-B and passes through ocular apertures 23A-B within eye scopes 12A-B along view paths 38A-B in the direction shown. In one embodiment, light sources 41A-B comprise infrared light sources and mirrors 18A-B comprise cold mirrors. The use of infrared light and cold mirrors allows the visible light generated by light sources 26A-B to be deflected by mirrors 18A-B while the infrared light passes through mirrors 18A-B and is allowed to continue towards monitoring apertures 20A-B. Achromatic lenses 16A-B can be used to focus the resulting images of eyes 52A-B for improved measurements of the pupillary reflexes. Still further, infrared light filters 30A-B can also be positioned between a measuring instrument and the patient's eyes 52A-B to ensure that only infrared light reaches the measuring instrument. In this case, infrared light filters 30A-B filter out any non-infrared light that may have passed through cold mirrors 18A-B. It is understood that infrared filters 30A-B could alternatively be provided as a single filter and can be located anywhere between patient's eyes 52A-B and the measuring instrument.

As shown in FIG. 1B, infrared light sources 41A-B may comprise a plurality of infrared lights 27 positioned around eyes 52A-B. For example, infrared light sources 41-B could be provided as a ring of infrared lights 27 positioned about the periphery of ocular apertures 23A-B of each eye scope 12A-B. In one embodiment, infrared lights 27 comprise light emitting diodes (LEDs). In addition, infrared lights 27 can be scuffed or the like so that the light generated by each infrared light 27 is dispersed about a greater surface area of the patient's pupil and as near axial as possible.

During testing, as the test eye 52A-B is exposed to the series of flashes, light sources 41A-B emit infrared light to both eyes 52A-B. The infrared light reflects off eyes 52A-B, passes through eye scopes 12A-B, and through monitoring apertures 20A-B, thereby allowing images of eyes 52A-B to be captured by recording mechanisms 36A-B. In one embodiment, recording mechanisms 36A-B comprise charged coupled devices with significant infrared sensitivity corresponding to the emission of infrared lights 27. However, other known recording means may be used. Further, recording mechanisms 36A-B can provide optical magnification of the images for improved analysis. In any case, recording mechanisms 36A-B record the pupillary reflexes of both eyes 52A-B simultaneously, and can output the recordings to computer system 42 via I/O mechanism 48. The recordings can be converted into recording data by software product 44. Software product 44 can be any number of products known in the art. Computer system 42 can process the recording data to generate an image 56 of one or both eyes 52A-B on video display 55. Further, computer system 42 and/or recording mechanisms 36A-B can determine if the detected pupillary reflexes meet required criteria. For example, only recorded pupillary reflexes that have required criteria comprising: a) measured culmination times of about 0.5 seconds, b) finite latencies, and c) no eye blinks during the recording interval may be accepted. The recording duration for the direct and consensual reflexes can be user-defined, however a duration of approximately one and a half seconds can be used as a default recording interval. If one or both of the pupillary reflexes do not meet all of the required criteria, the eye can be re-exposed to the flash after a suitable interval (e.g., ten seconds).

The recording data can also be processed to generate image data/graphs 57 for display on video display 55. For example, the dimension of one or both pupils 54A-B can be displayed in a graph as a function of time. In one embodiment, software product 44 identifies the pupil component of the image and counts the number of pixels in the pupil component of the image to determine the dimensions (e.g., diameter) of pupils 54A-B. Alternatively, software product 44 can implement a scanning line technique with infrared light, as disclosed in U.S. Pat. No. 3,533,683 to Stark et al., hereby incorporated by reference. In any event, once the dimensions of pupils 54A-B are determined, the presence of an ocular dysfunction in one or both of eyes 52A-B can be determined.

Figure 5:
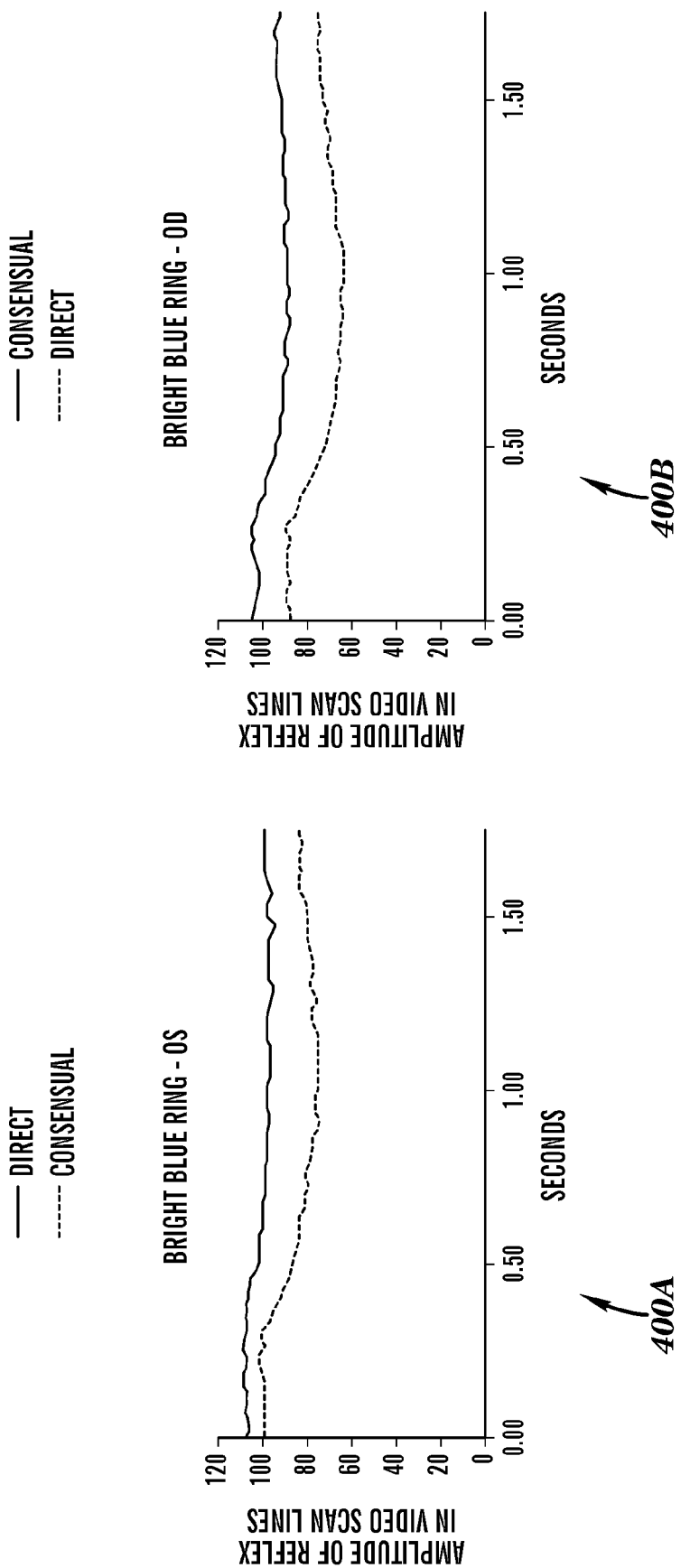
FIG. 5A shows a recording of direct and consensual pupillary reflexes evoked by a flash exposed to the left eye of a patient according to one aspect of the invention.
FIG. 5B shows a recording of direct and consensual pupillary reflexes evoked by a flash exposed to the right eye of a patient according to another aspect of the invention.

FIGS. 5A and 5B show illustrative graphs 400A-B generated from the recording data that can be displayed on video display 55 for analysis by an operator. Graph 400A represents recording data when a left eye was exposed to the flash, and graph 400B represents recording data when a right eye was exposed to the same flash. In both cases, the flash comprised a bright blue beam of light. In each graph 400A-B, the video frames that were recorded in a time interval of 1.75 seconds following the onset of a flash were analyzed to generate the data shown. In this case, the pupil size is shown as a number of video scan lines obtained from each video frame. In each graph 400A-B, data for both the exposed eye (direct) as well as the other eye (consensual) are charted. Graphs 400A-B allow an operator to visually analyze the pupillary reflexes of both eyes to the exposed flash.

Returning to FIG. 1B, the system further includes a control panel 50 having one or more control adjusters 51. Control adjusters 51 allow an operator to adjust the video features (e.g., height and width) of an image as it appears on the video display 55 and to define a region of interest in the video image. In particular, an operator can adjust the vertical and/or horizontal dimensions of a window of interest of the video display 55 and the location with reference to the corneal region of the eye to be captured by the recording mechanisms 36A-B.

Electronic overlay board 46 can also be included in computer system 42 for producing an electronic overlay. The electronic overlay can be used to further limit the fields of view of recording mechanisms 36A-B. The overlay feature can be enabled by overlay board 46 in computer system 42 and can be implemented using technology known in the art. The electronic overlay can also be positioned by one or more control adjusters 51. Control adjusters 51 can allow a user to customize the field of view for a particular patient as the user views images 56 of eyes 52A-B on video display 55. Specifically, once a patient is properly positioned so pupils 54A-B are in the field of view, an operator can view video display 55 and adjust (position and size) the overlay 60 until it only overlays pupils 54A-B of the patient. Once the overlay is in its proper position, and the threshold is set, the image is ready for processing. In one embodiment, overlay area 60 is circular and can be sized to fit within the pupil. A narrower overlay may be used as long as it covers, i.e. can measure, the pupil diameter.

Figure 3:
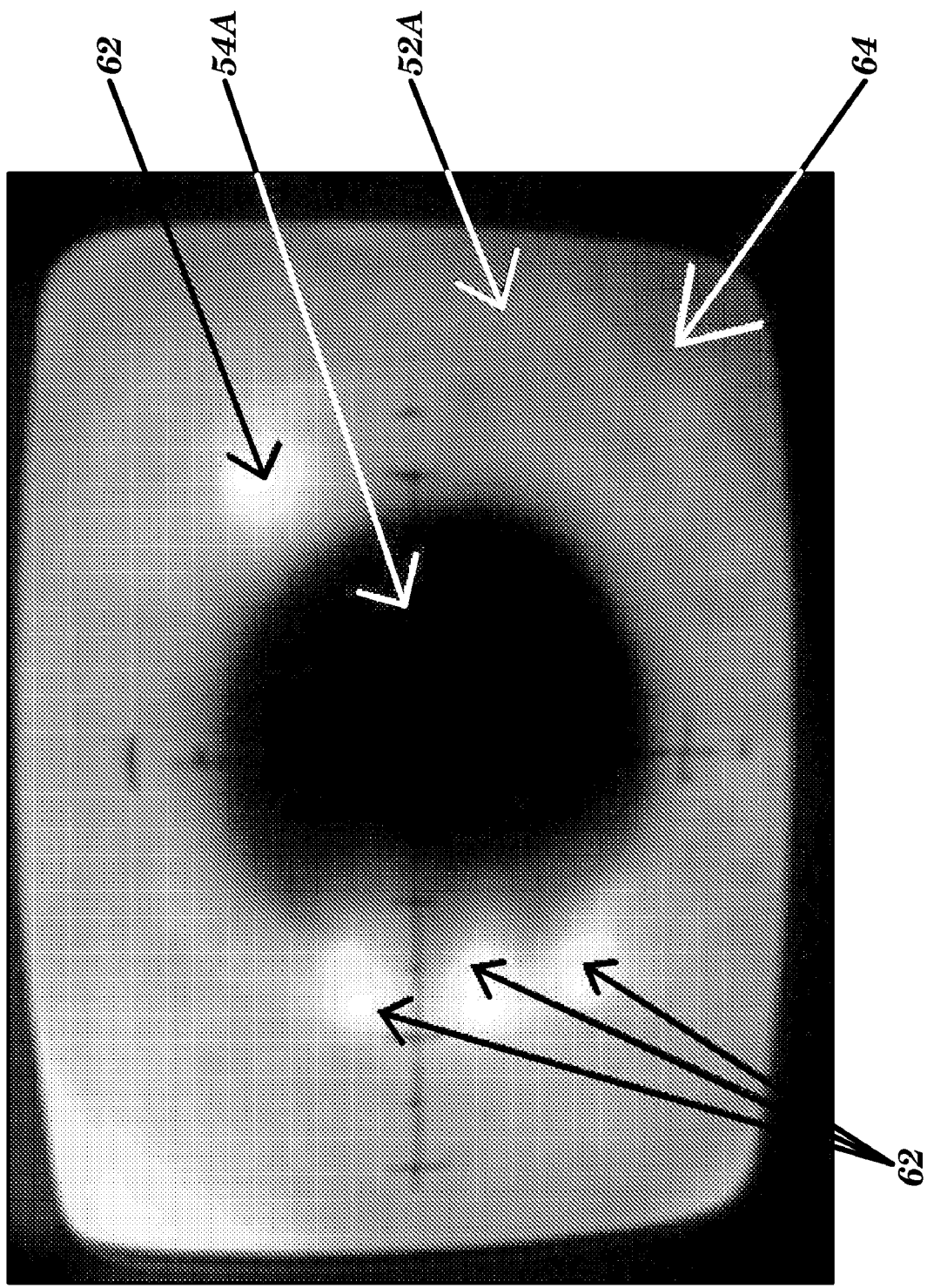
FIG. 3 shows a recorded image of an eye according to yet another aspect of the invention.
Figure 4:
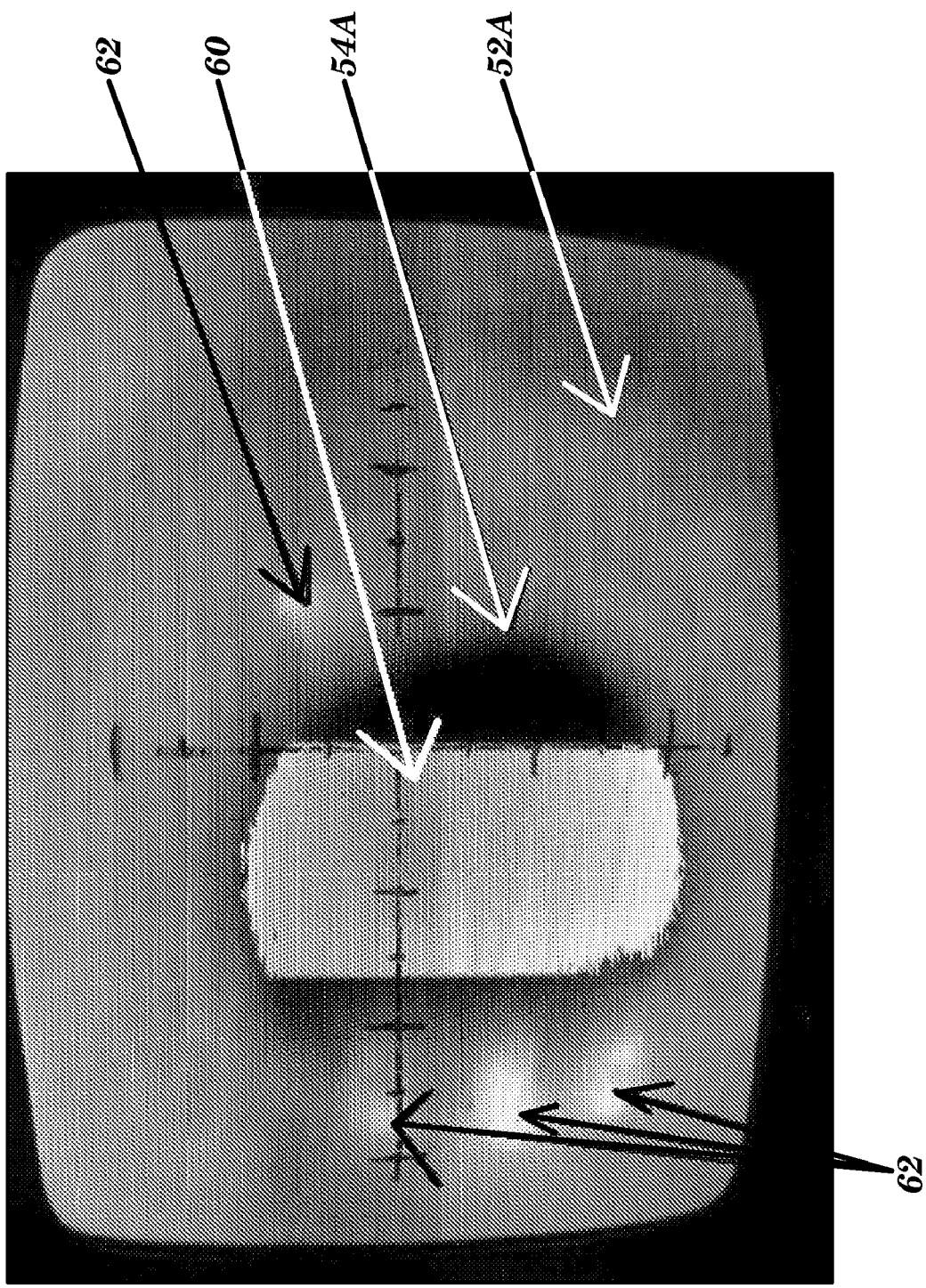
FIG. 4 shows a recorded image of an eye that includes an overlay feature according to another aspect of the invention.

For example, FIG. 3 shows an image of eye 52A without the overlay features. As shown, the field of view 64 extends beyond the pupillary boundary (the periphery of the pupil 54A) and includes noise 62. For example, noise 62 may comprise a series of bright points that may be generated when infrared lights 27 (FIG. 1B) are used to illuminate eye 52A. In any event, noise 62 may interfere with the accurate analysis of the eye image and its corresponding dimensional data. As shown in FIG. 4, the use of an electronic overlay limits the field of view of recording mechanism 36A (FIG. 1A) to an overlay area 60 that is defined primarily by pupil 54A, thereby excluding noise 62 and/or any other extraneous features.

Figure 6:
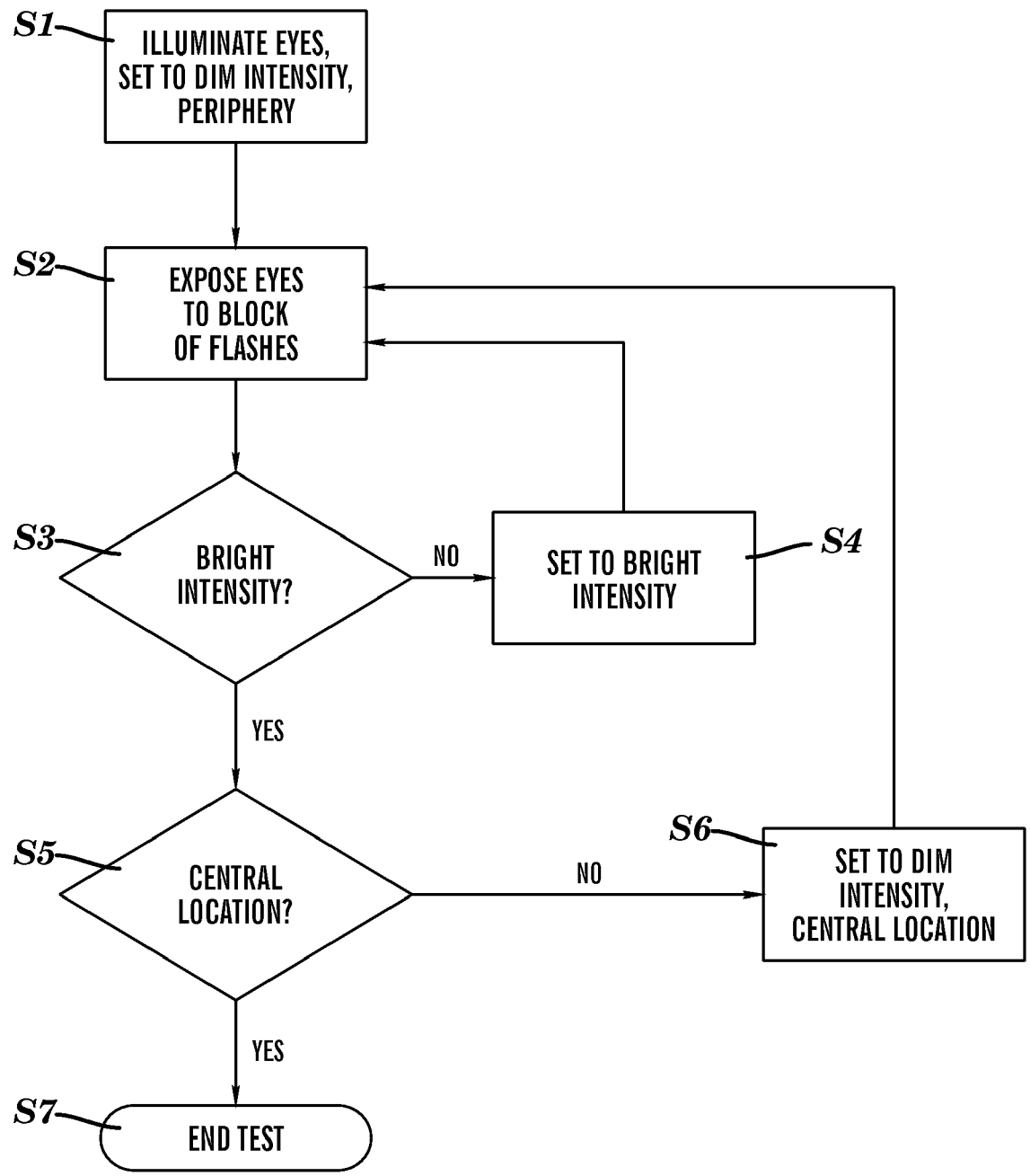
FIG. 6 shows illustrative method steps according to one aspect of the invention.

FIG. 6 shows illustrative method steps for testing eyes 52A-B (FIG. 1A) according to one embodiment of the invention. In the embodiment shown, eyes 52A-B are exposed to a "block" of flashes in step S2. A block of flashes comprises a series of flashes to which each eye 52A-B of the patient is exposed. In one embodiment, a first eye can be exposed to the series of flashes, followed by the second eye being exposed to the same series of flashes. Each flash in the series of flashes varies from the other flashes in the series by at least one of: location in the visual field, luminosity, and/or chromatically. In the embodiment shown, each flash in the series of flashes to which each eye is exposed in step S2 varies chromatically from the other flashes in the series. For example, the series of flashes can comprise four flashes, in which the first flash is red, followed in order by green, blue, and yellow flashes. Further, the series of flashes is repeated for each combination of two settings for luminosity (i.e., dim and bright), and two locations for the field of view (i.e., periphery and central). It is understood, however, that numerous variations are possible.

Figure 7:
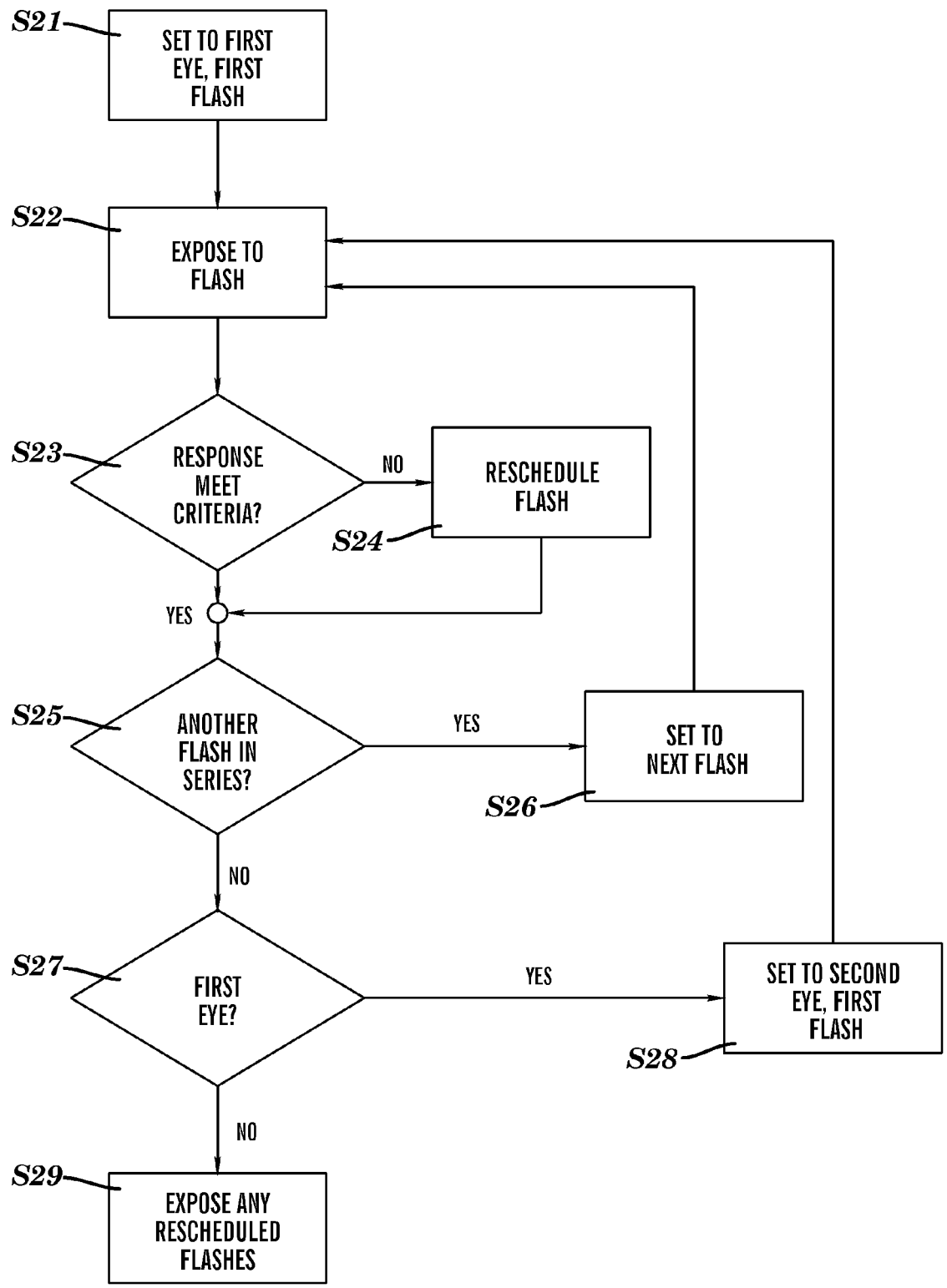
FIG. 7 shows illustrative method steps according to another aspect of the invention.

In any event, once a patient is properly positioned proximate device 10 (FIG. 1A) for testing, eyes 52A-B can be illuminated using light sources 41A-B (FIG. 1A) in step S1, and the settings for a first block of flashes are set so that each flash has a dim intensity, and a location in a periphery of the visual field. In step S2, the eyes are exposed to the block of flashes. FIG. 7 shows illustrative steps used to expose the eyes to the block of flashes. In this case, each flash in the series of flashes varies chromatically from the other flashes in the same series of flashes. In step S21, device 10 (FIG. 1A) is set to expose a first eye to the first flash in the series of flashes. In step S22, the eye is exposed to the flash. In step S23, it is determined if the pupillary reflexes that were detected by, for example, recording mechanisms 36A-B (FIG. 1A) include the required criteria (e.g., eyes did not blink). If the pupillary reflexes do not meet the required criteria, the flash is rescheduled in step S24 to be re-exposed at the end of the block. In step S25, it is determined if there are any additional flashes in the series. If additional flashes remain, device 10 is set to expose the next flash in step S26, and flow returns to step S22 where the flash is exposed. Once all flashes in the series have been exposed, it is determined in step S27 if both eyes have been exposed to the series. If only the first eye has been exposed, flow continues to step S28 in which device 10 is set to expose the second eye to the first flash in the series, and flow returns to step S22 where the flash is exposed. Once the series of flashes has been exposed to both eyes, flow continues to step S29 wherein any rescheduled flashes are re-exposed in a similar manner. To re-expose each rescheduled flash, the eye and the corresponding flash in the sequence are stored and device 10 is set appropriately between each flash. It is understood that the method steps are only illustrative, and various alternatives are possible. For example, a flash can be rescheduled to occur at the end of the series of flashes, or the flash could be re-exposed as the next flash.

Returning to the embodiment shown in FIG. 6, once the eyes have been exposed to the block of flashes in step S2, it is determined what intensity was used in step S3. If the dim setting for luminosity was used, then the luminosity is set to the bright setting in step S4, and flow returns to step S2 wherein the eyes are exposed to the block of flashes using the new luminosity setting. If the bright luminosity setting was used, the location setting that was used for the block of flashes is determined in step S5. If the periphery location was used, then the location setting is changed to the central location in step S6. Additionally, the luminosity setting is changed back to dim so that both the dim and bright settings will be used for the new location. Once the eyes have been exposed to the block of flashes having bright intensity and located in the central location of the field of view, the test is ended in step S7.

In one embodiment, each series of flashes comprises four flashes (e.g., red, green, blue, yellow). Consequently, each block of flashes would comprise eight flashes. Further, each flash in each series of flashes can be spaced from a previous flash by approximately ten seconds. When repeated for each combination of two luminosity settings, and two different locations in the field of view, each block of flashes would be performed four times. As a result, the entire test (i.e., thirty-two flashes) can be run in approximately five minutes (without any rescheduled flashes).

As previously noted, the recorded pupillary reflexes can be processed to detect the presence of an ocular dysfunction. For example, the pupil sizes can be used to determine the Relative Afferent Pupillary Defects (RAPD) evoked by each flash. By exposing both eyes to the same series of flashes, and simultaneously measuring the direct and consensual pupillary reflexes for each flash, two values for the RAPD can be calculated. First, when the left eye was exposed to the series of flashes, the RAPD for each flash can be calculated by subtracting the direct pupillary reflex of the left eye (OSD) from the consensual pupillary reflex of the right eye (ODC), or ODC-OSD. Second, the RAPD can be calculated when the right eye was exposed to the same series of flashes. In this case, the RAPD for each flash can be calculated by subtracting the consensual pupillary reflex of the left eye (OSC) from the direct pupillary reflex of the right eye (ODD), or ODD-OSC. A non-zero result for either of the calculations indicates that an ocular dysfunction is present. The size of the difference provides some indication of the extent of the dysfunction. Further, the sign of the difference indicates the eye in which the defect is present. For example, since the left eye was subtracted from the right eye for each flash in the table below, a positive value indicates a left afferent defect (LA) and a negative value indicates a right afferent defect (RA).

| RAPD Magnitudes and Their Classification as Left or Right Afferent Defects as Determined from Reflex Amplitudes | | | | |
|---|---|---|---|---|
| S - POAG | Red | Yellow | Green | Blue |
| Bright Disk | | | | |
| ODC - OSD defect | 0.45 (LA) | 0.30 (LA) | 0.30 (LA) | 1.15 (LA) |
| ODD - OSC defect | 1.45 (LA) | −0.25 (RA) | −1.25 (RA) | 1.35 (LA) |
| Bright Ring | | | | |
| ODC - OSD defect | 0.95 (LA) | −2.00 (RA) | 2.80 (LA) | 4.65 (LA) |
| ODD - OSC defect | 2.65 (LA) | −3.30 (RA) | 1.25 (LA) | 1.30 (LA) |
| Dim Disk | | | | |
| ODC - OSD defect | −0.95 (RA) | 0.55 (LA) | 0.40 (LA) | −2.10 (RA) |
| ODD - OSC defect | 0.00 | 0.25 (LA) | 2.30 (LA) | −1.20 (RA) |
| Dim Ring | | | | |
| ODC - OSD defect | 2.85 (LA) | 0.20 (LA) | 1.90 (LA) | 0.65 (LA) |
| ODD - OSC defect | 5.65 (LA) | −0.15 (RA) | 2.10 (LA) | 5.30 (LA) |

A multivariate mode of analyses can also be used to further discriminate between the various optic dysfunctions of, for example, patients diagnosed with the glaucoma group of diseases. For example, the Pearson product moment correlation coefficients between the matrices of the RAPDs of any number of selected patients' eyes can be calculated so as to determine the extent of the resemblance between the pattern of RAPDs of each of these patients' individual eye or eyes. In order to obtain the best results, the flashes can be provided in the same, or as close to the same as possible, sequence to each patient. A high correlation between the ocular dysfunctions of a first patient and a second patient known to have a particular ocular disorder may indicate that the first patient also has the ocular disorder. When data from numerous patients is used for each disorder, a set of inter-correlation matrices can be constructed as shown in FIG. 8. The inter-correlation matrices can provide the ability to compare relevant correlations between a test patient's data and that of index patients having various diagnosed ocular disorders. The inter-correlation matrices allow precise quantitative assessment of the resemblance of the data recorded for a test patient to the data recorded for patients clinically diagnosed as having various ocular dysfunctions.

It is understood that the invention can be realized in hardware, software, or a combination of hardware and software.

Any kind of computer/server system(s)—or other apparatus adapted for carrying out the methods described herein—is suited. A typical combination of hardware and software could be a general-purpose computer system with a computer program that, when loaded and executed, carries out the respective methods described herein. Alternatively, a specific use computer, containing specialized hardware for carrying out one or more of the functional tasks of the invention, could be utilized. The invention can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method comprising:
    exposing a first eye of a patient to at least one series of flashes, wherein each of the at least one series of flashes includes flashes that vary chromatically from the other flashes in the same series of flashes; and
    concurrently recording image data of the first eye and a second eye of the patient during the exposing.

2. The method of claim 1, further comprising repeating the exposing and recording for the second eye.

3. The method of claim 1, further comprising illuminating the first and second eyes prior to the exposing.

4. The method of claim 1, further comprising measuring pupillary reflexes of the first eye and the second eye as a result of the exposing based on the image data for the first eye and the second eye.

5. The method of claim 1, wherein at least one flash in each of the at least one series of flashes is a red flash.

6. The method of claim 5, wherein the red flash has no photochromatic interval.

7. The method of claim 1, wherein at least one flash in each of the at least one series of flashes provides a uniformly intense illumination of a portion of a visual field of the first eye.

8. The method of claim 1, further comprising generating a set of graphs for presentation on a video display based on the image data.

9. The method of claim 1, wherein at least one flash in each of the at least one series of flashes is a white flash.

10. The method of claim 1, wherein each flash in each of the at least one series of flashes comprises a duration less than a start of a release phase of a pupillary reflex of the first eye in response to the flash.

11. The method of claim 10, wherein each flash in each of the at least one series of flashes is separated from an adjacent flash in the same series of flashes by approximately ten seconds.

12. The method of claim 1, wherein each of the at least one series of flashes includes at least four flashes.

13. A system comprising:
    at least one light source configured to generate light of varying chromaticity;
    a component configured to direct the generated light towards one of a pair of ocular apertures;
    at least one recording mechanism configured to concurrently record image data of a first eye and a second eye located adjacent to the pair of ocular apertures; and
    a component configured to generate a first series of flashes using the at least one light source, wherein the first series of flashes includes flashes that vary chromatically from the other flashes in the same series of flashes.

14. The system of claim 13, further comprising an interocular distance adjuster configured to adjust a distance between the pair of ocular apertures.

15. The system of claim 13, further comprising at least one infrared light source configured to illuminate the first eye and the second eye with infrared light.

16. The system of claim 13, further comprising a component configured to measure a direct pupillary reflex of one of the first eye or the second eye and a consensual pupillary reflex of the other of the first eye or the second eye as a result of the one of the first eye or the second eye being exposed to a flash based on image data of the first eye and the second eye recorded during and immediately after the flash.

17. The system of claim 16, further comprising a component configured to generate a graph for presentation on a video display based on the measured pupillary reflexes.

18. The system of claim 16, further comprising a component configured to determine whether the direct pupillary reflex and the consensual pupillary reflex were detected in the image data.

19. A system comprising:
    a component configured to generate at least one series of flashes for exposure to a first eye of a patient, wherein each of the at least one series of flashes includes flashes that vary chromatically from the other flashes in the same series of flashes; and
    at least one recording mechanism configured to concurrently record image data of the first eye and a second eye of the patient during the at least one series of flashes.

20. The system of claim 19, wherein the component configured to generate includes:
    at least one light source configured to generate light of varying chromaticity; and
    a component configured to direct the generated light towards one of a pair of ocular apertures.

21. The system of claim 20, further comprising an interocular distance adjuster configured to adjust a distance between the pair of ocular apertures.

22. The system of claim 19, further comprising at least one infrared light source configured to illuminate the first eye and the second eye with infrared light during the at least one series of flashes.

23. The system of claim 19, further comprising a component configured to measure pupillary reflexes of the first eye and the second eye as a result of the at least one series of flashes based on the image data for the first eye and the second eye.

24. The system of claim 19, further comprising a component configured to determine whether pupillary reflexes of the first eye and the second eye in response to a flash in the at least one series of flashes were detected in the image data.

* * * * *